United States Patent
Dees et al.

(10) Patent No.: US 12,186,194 B2
(45) Date of Patent: Jan. 7, 2025

(54) ANATOMICALLY SHAPED AUGMENTS

(71) Applicant: Smith & Nephew, Inc., Memphis, TN (US)

(72) Inventors: Roger Ryan Dees, Senatobia, MS (US); Jeffrey N. Yeager, Nesbit, MS (US); Angela Mines, Arlington, TN (US); Paul Charles Crabtree, Nesbit, MS (US)

(73) Assignee: Smith & Nephew, Inc., Memphis, TN (US)

( * ) Notice: Subject to any disclaimer, the term of this patent is extended or adjusted under 35 U.S.C. 154(b) by 1005 days.

(21) Appl. No.: 17/142,754

(22) Filed: Jan. 6, 2021

(65) Prior Publication Data

US 2021/0121292 A1    Apr. 29, 2021

Related U.S. Application Data

(63) Continuation of application No. 15/572,959, filed as application No. PCT/US2016/032361 on May 13, 2016, now Pat. No. 10,912,649.

(Continued)

(51) Int. Cl.
*A61F 2/30* (2006.01)
*A61B 17/72* (2006.01)
(Continued)

(52) U.S. Cl.
CPC .......... *A61F 2/30734* (2013.01); *A61B 17/72* (2013.01); *A61F 2/3859* (2013.01);
(Continued)

(58) Field of Classification Search
CPC .... A61F 2/30734; A61F 2/3859; A61F 2/389; A61F 2002/30594; A61F 2002/30736;
(Continued)

(56) References Cited

U.S. PATENT DOCUMENTS 4,846,839 A * 7/1989 Noiles ................ A61F 2/38
                                                 623/23.46
7,291,174 B2 * 11/2007 German ............ A61F 2/30734
                                                 623/23.46
(Continued)

FOREIGN PATENT DOCUMENTS

CN    103690277 A    4/2014
CN    103830022 A    6/2014
(Continued)

OTHER PUBLICATIONS

Office Action for JP Application No. 2017-559031, mailing date Jan. 18, 2021, original and translated document, 13 pages.
(Continued)

*Primary Examiner* — Jerrah Edwards
*Assistant Examiner* — Christine L Nelson
(74) *Attorney, Agent, or Firm* — KDW Firm PLLC

(57) ABSTRACT

Augments for implantation of an orthopedic implant device in a bone. A distal end of an outer portion of the augment can have a shape that is configured to generally conform to the shape of a metaphyseal-diaphyseal junction of an intramedullary canal of the bone. Further, a proximal end of the outer portion of the augment has a shape that is configured to generally conform to a shape of the metaphyseal region of the intramedullary canal. Additionally, the shape of the outer portion at the distal end can be separated from the shape of the outer portion at the proximal end by a distance that is approximately equal to the distance between the metaphyseal-diaphyseal junction and the metaphyseal region of the intramedullary canal.

20 Claims, 12 Drawing Sheets

Related U.S. Application Data

(60) Provisional application No. 62/161,018, filed on May 13, 2015.

(51) Int. Cl.
*A61F 2/38* (2006.01)
*A61F 2/46* (2006.01)

(52) U.S. Cl.
CPC .... *A61F 2/389* (2013.01); *A61F 2002/30215* (2013.01); *A61F 2002/30449* (2013.01); *A61F 2002/30594* (2013.01); *A61F 2002/30736* (2013.01); *A61F 2002/30738* (2013.01); *A61F 2002/30878* (2013.01); *A61F 2002/30897* (2013.01); *A61F 2002/4631* (2013.01)

(58) Field of Classification Search
CPC .. A61F 2002/30738; A61F 2002/30878; A61F 2002/4631; A71B 17/72
See application file for complete search history.

(56) References Cited

U.S. PATENT DOCUMENTS

| | | | |
|---|---|---|---|
| 8,424,183 B2* | 4/2013 | Thomas | A61F 2/38 623/20.16 |
| 9,011,458 B2* | 4/2015 | Matyas | A61F 2/4603 606/86 R |
| 9,301,857 B2 | 4/2016 | Matyas et al. | |
| 9,532,879 B2 | 1/2017 | Lieberman et al. | |
| 10,335,284 B2 | 7/2019 | Landon et al. | |
| 2004/0049286 A1 | 3/2004 | German et al. | |
| 2004/0162619 A1 | 8/2004 | Blaylock et al. | |
| 2012/0041564 A1 | 2/2012 | Landon | |
| 2013/0172892 A1 | 7/2013 | Servidio et al. | |
| 2013/0304221 A1 | 11/2013 | Blaylock et al. | |
| 2014/0081411 A1* | 3/2014 | Lieberman | A61F 2/389 623/20.15 |
| 2014/0277528 A1 | 9/2014 | Mines et al. | |
| 2014/0277567 A1 | 9/2014 | Collazo et al. | |

FOREIGN PATENT DOCUMENTS

| | | |
|---|---|---|
| EP | 1396240 A2 | 3/2004 |
| EP | 2679201 A1 | 1/2014 |
| EP | 2130516 B1 | 3/2014 |
| JP | 2014008411 A | 1/2014 |
| JP | 2014061385 A | 4/2014 |
| WO | 2016183446 A1 | 11/2016 |

OTHER PUBLICATIONS

Australian Examination report No. 2 for standard patent application No. 2016260425, dated Mar. 26, 2021, 4 pages.
Examination Report No. 1 for Australian Patent Application No. 2016260425, mailed Jan. 2, 2020.
Notice of Reasons for Rejection for Japanese Patent Application No. 2017-559031, mailed Feb. 3, 2020.
Chinese Search Report; State Intellectual Property Office, Peoples Republic of China; Chinese Patent Application No. 201680027800. X; Dec. 27, 2018; 7 pages.
Chinese Office Action (1st); State Intellectual Property Office, Peoples Republic of China; Chinese Patent Application No. 201680027800 X; Dec. 27, 2018; 24 pages.
Second Office Action for Chinese Patent Application No. 201680027800. X, mailed Sep. 23, 2019.
Third Office Action for Chinese Patent Application No. 201680027800. X, mailed Jun. 2, 2020.
International Search report; European Patent Office; International Application No. PCT/US2016/032361; Aug. 9, 2016; 5 pages.
Written Opinion of the International Searching Authority; European Patent Office; International Application No. PCT/US2016/032361; Aug. 9, 2016; 5 pages.

* cited by examiner

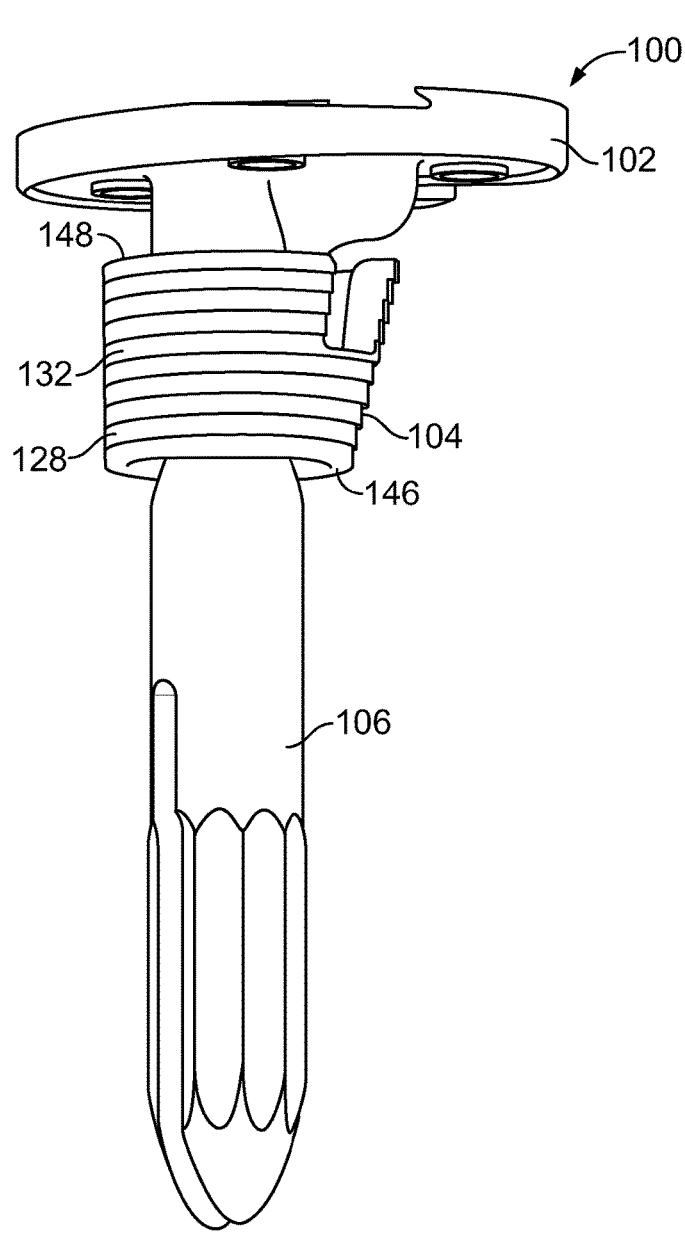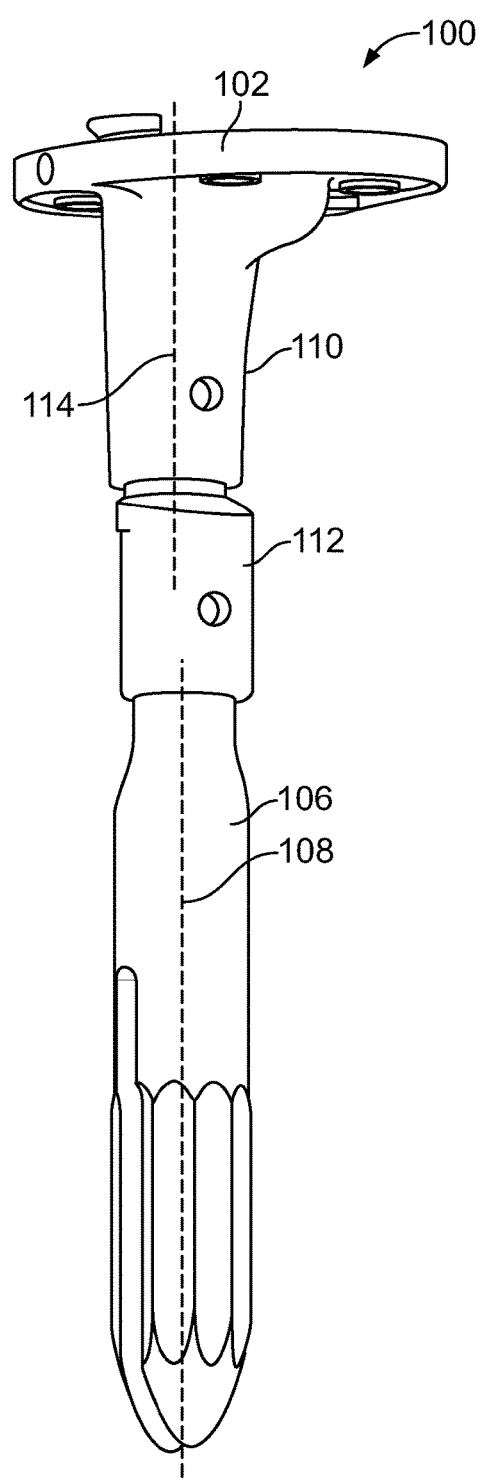
FIG. 3
FIG. 4

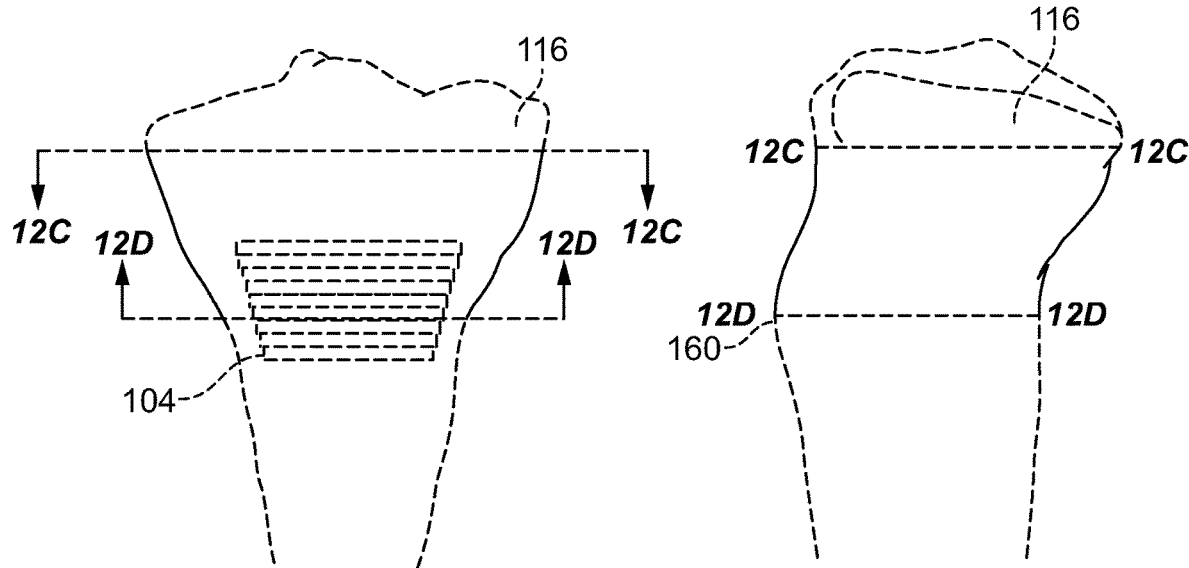
FIG. 12A  FIG. 12B
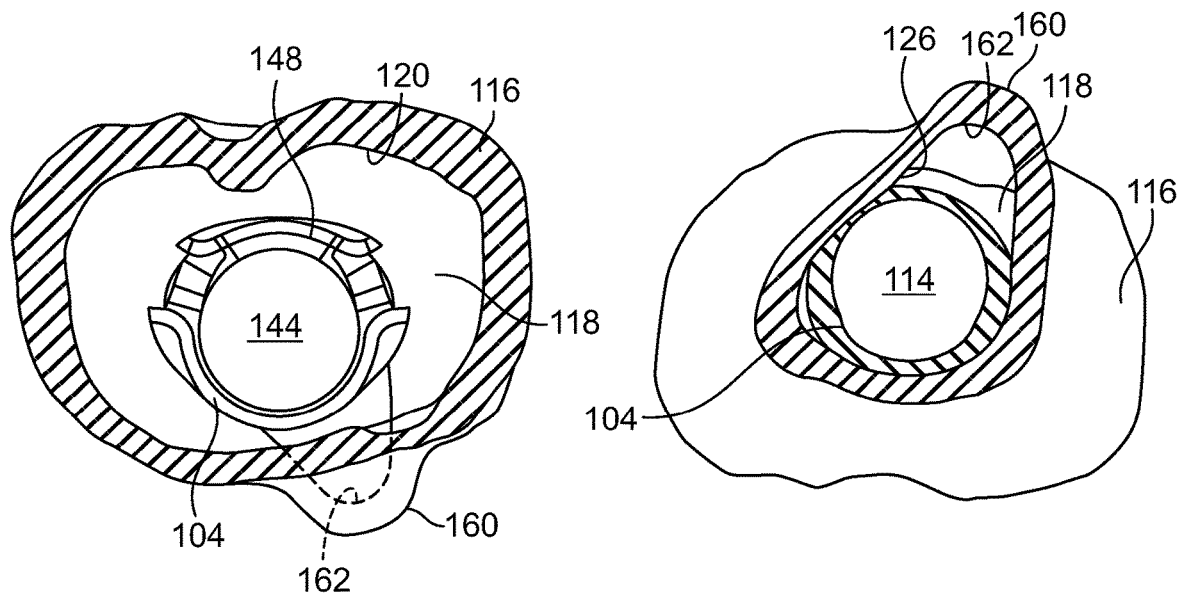
FIG. 12C  FIG. 12D

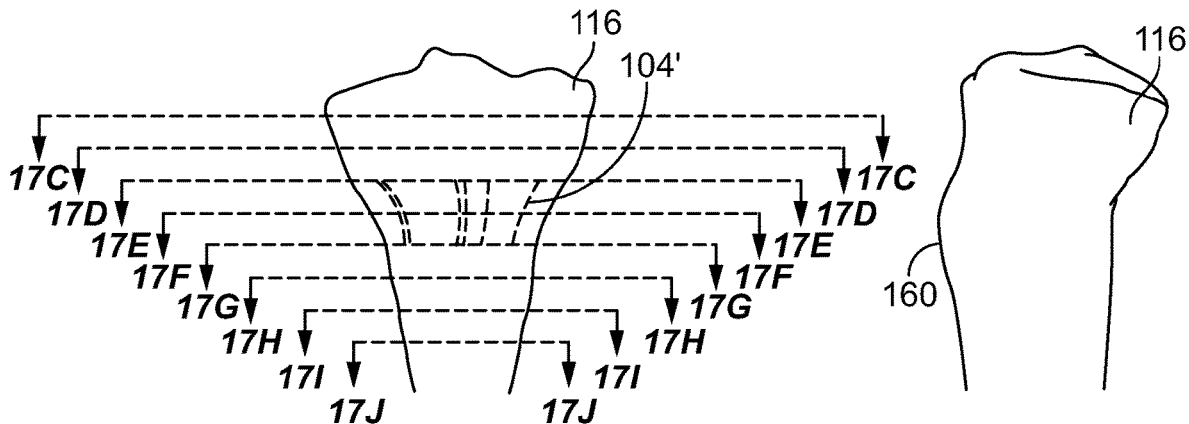
FIG. 17A  FIG. 17B
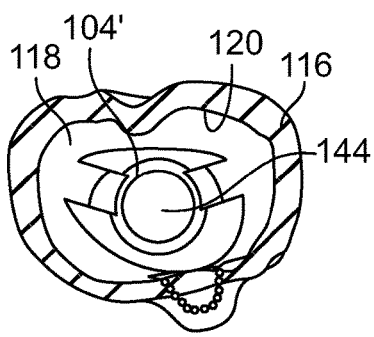 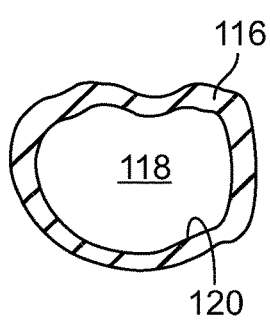 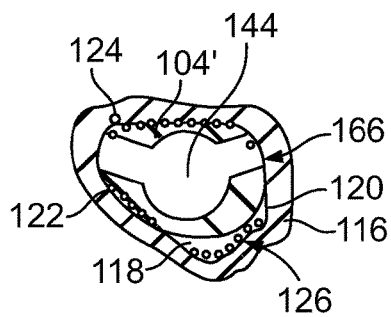
FIG. 17C  FIG. 17D  FIG. 17E
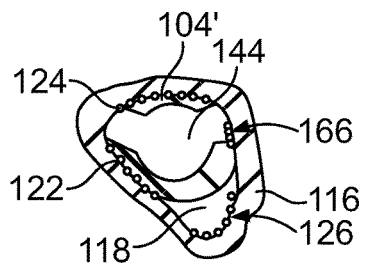 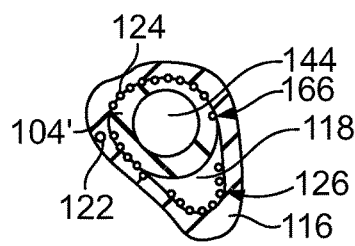 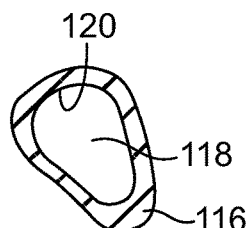
FIG. 17F  FIG. 17G  FIG. 17H
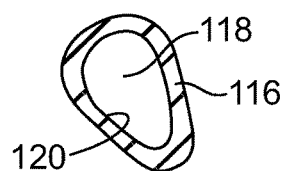 
FIG. 17I  FIG. 17J

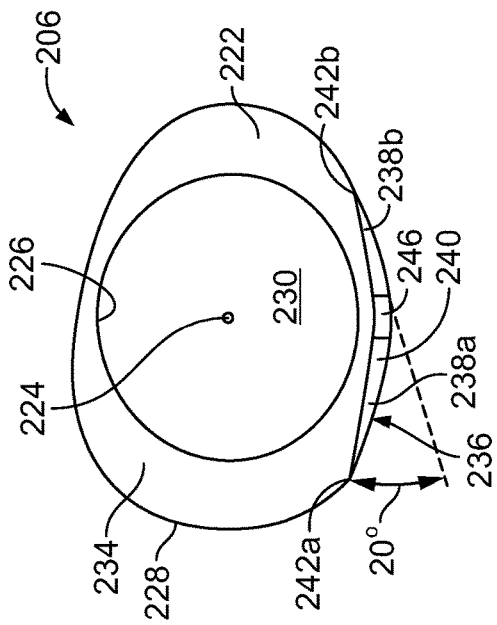
FIG. 22
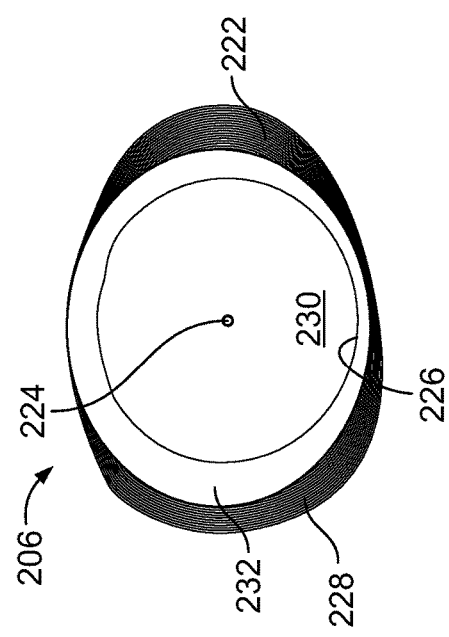
FIG. 23
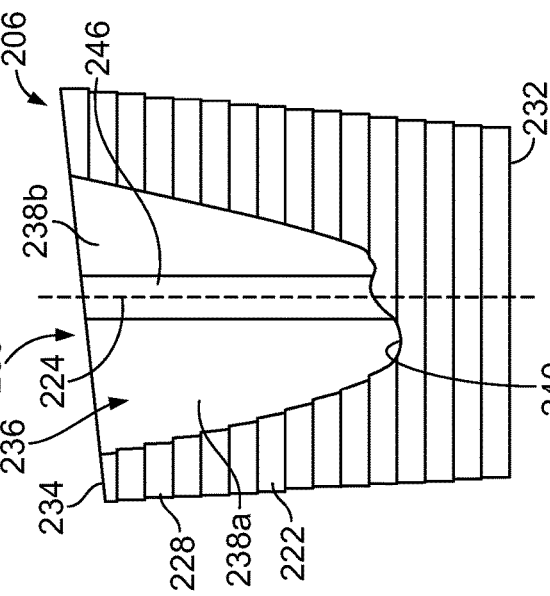
FIG. 24
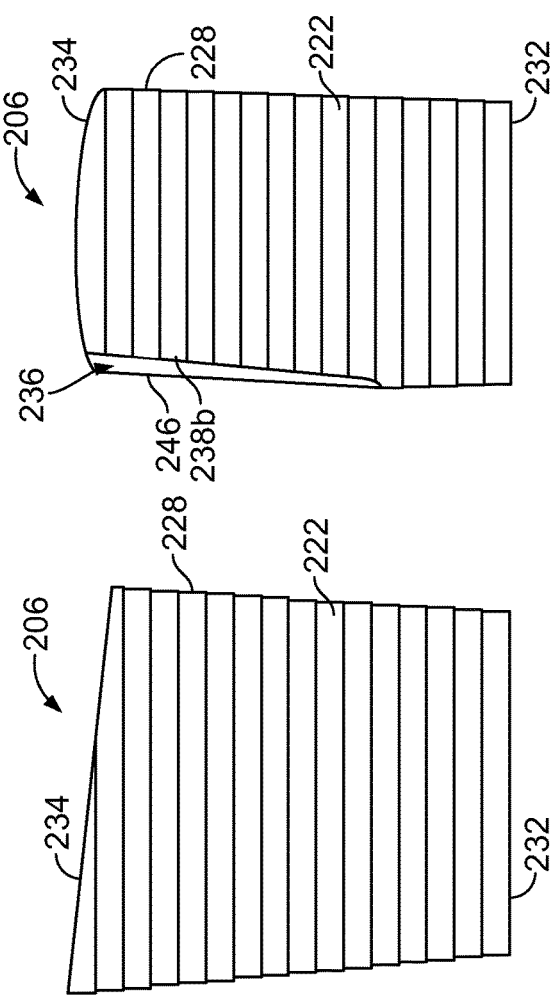
FIG. 25
FIG. 26

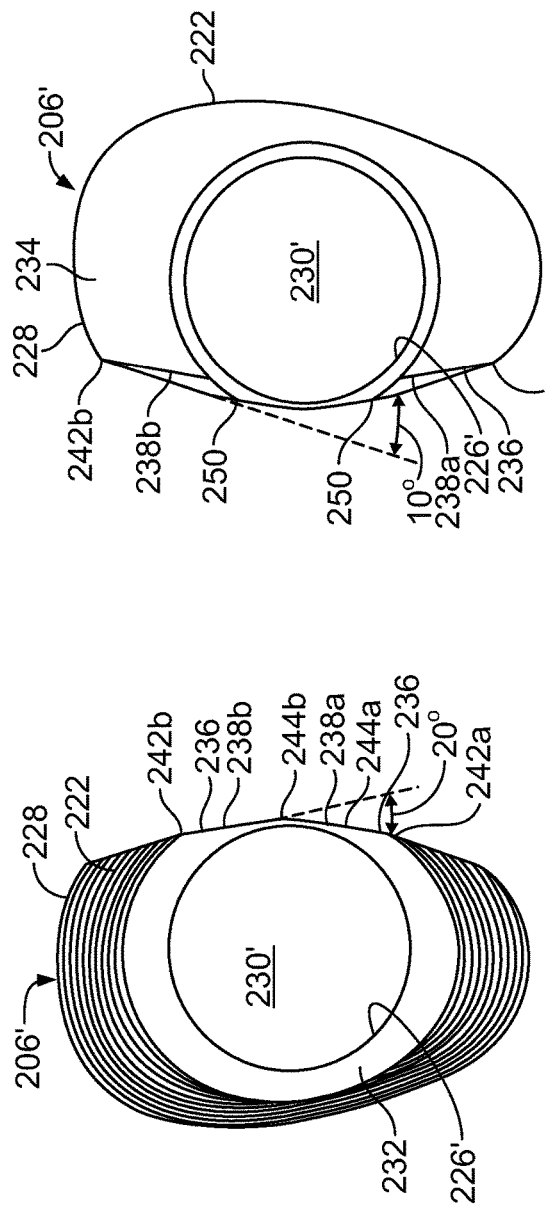
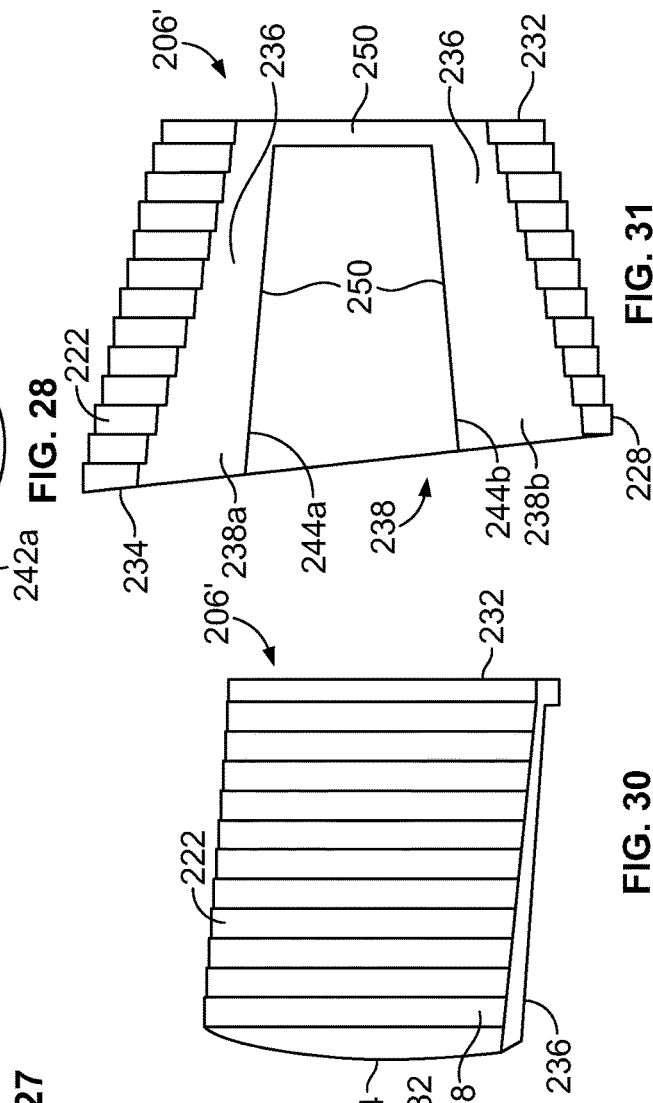
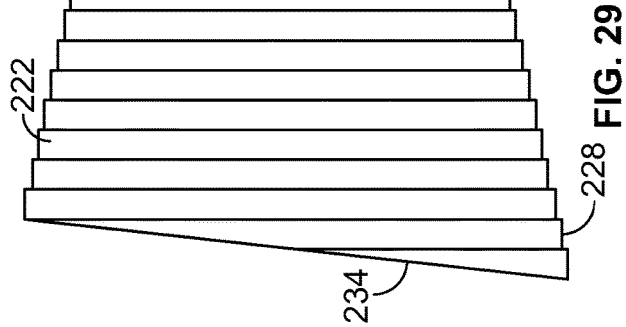

ANATOMICALLY SHAPED AUGMENTS

CROSS-REFERENCE TO RELATED APPLICATIONS

The present application is a continuation of pending U.S. patent application Ser. No. 15/572,959, filed Nov. 9, 2017, entitled "Anatomically Shaped Augments", which application is a U.S. National Phase of International PCT Application No. PCT/US2016/032361, filed May 13, 2016, which claims the benefit of U.S. Provisional Patent Application No. 62/161,018, filed on May 13, 2015, the contents of each application hereby incorporated herein by reference in their entirety.

BACKGROUND

Embodiments of the present application generally relate to orthopedic augments. More particularly, but not exclusively, embodiments of the present application relate to anatomically shaped orthopedic alignments that are configured to prevent or minimize unequal loading conditions and provide enhanced flexibility in placement within the associated bone canal.

Metaphyseal and/or diaphyseal augments typically assist in preventing loosening and/or subsidence of an articular component, such as, for example, an implanted tibia baseplate. Such augments can help distribute loads exerted on or by the articular implant through the bone, with the articular component maintaining fixation, which can result in a longer implant life.

One of the primary forces attributed to early failures of orthopedic implants, particularly in the tibia, is torsional stress. Moreover, torsional stresses can shear the articular implant-bone interface (cemented or un-cemented) apart, which can facilitate premature or early failure of the implant. Other forces, such as shear forces, can also contribute to similar premature or early failure of the articular implant-bone interface. Additionally, compressive loads, particularly unequal loads to a median plane (i.e. medial loading) of the articular implant-bone interface, can also cause subsidence and early failures of the articular implant.

Additionally, too much cortical contact with the augment can, as a consequence of carrying too much of the load, stress shield the host bone of the bone interface. Such situations can result in bone resorption, which can contribute to early failure of the implant. Additionally, unequal cortical contact due to lack of conformity or fit can load a particular region of the bone, and thereby relieve the articular implant-bone interface in a similar region. In at least certain situations, areas subjected to such unequal loads or contact can exhibit characteristics similar to a fulcrum, which can facilitate bone-interface failures for both the augment and the articular implant.

BRIEF SUMMARY

An aspect of the present application is an augment for implantation of an orthopedic implant device in a bone, the augment having an augment wall that includes an outer portion and an inner portion. The inner portion of the augment wall defines an inner region of the augment that is sized to receive placement of one or more components of the orthopedic implant device. A distal end of the outer portion has a first shape that is configured to generally conform to the shape of a metaphyseal-diaphyseal junction of a canal of the bone. Additionally, a proximal end of the outer portion has a second shape that is configured to generally conform to a shape of the metaphyseal region of the canal of the bone. Further, the first shape has different shape and size than the second shape.

Another aspect of the present application is an augment for implantation of an orthopedic implant device in a bone, the augment having an augment wall that includes a posterior curvature portion and an anterior-medial portion. The posterior curvature portion at a first end of the augment is shaped to generally conform to a posterior curvature wall of a canal of the bone at a metaphyseal-diaphyseal junction of the canal, while the posterior curvature portion at a second end of the augment is shaped to generally conform to a posterior curvature wall of the canal at a metaphyseal region of the canal. Further, the anterior-medial portion at the first end of the augment is shaped to generally conform to an anterior-medial wall of the canal at the metaphyseal-diaphyseal junction, while the anterior-medial portion at the second end of the augment is shaped to generally conform to the anterior-medial wall at the metaphyseal region of the canal. Additionally, the shape of the posterior curvature portion at the metaphyseal region is different than the shape of the anterior-medial portion at the metaphyseal region.

BRIEF DESCRIPTION OF THE DRAWINGS

The description herein makes reference to the accompanying figures wherein like reference numerals refer to like parts throughout the several views.

FIG. 3 illustrates an isometric view of the tibial implant device shown in FIG. 1.

FIG. 4 illustrates an isometric view of a tibial implant device having an offset/angled coupler.

FIG. 12A illustrates an anterior view of a proximal tibia bone with an exemplary symmetrical tibial augment of the present application implanted in the intramedullary canal.

FIG. 12B illustrates a medial-lateral view of the proximal tibia bone that is illustrated in FIG. 12A.

FIG. 12C illustrates a slice view of the proximal tibia bone and exemplary symmetrical tibial augment along line 12C-12C from FIG. 12A.

FIG. 12D illustrates a slice view of the proximal tibia bone and exemplary symmetrical tibial augment along line 12D-12D from FIG. 12A.

FIGS. 17A and 17C-17J illustrate, respectively, an anterior view and associated slice views of a proximal tibia bone with an exemplary asymmetrical tibial augment of the present application implanted in the intramedullary canal.

FIG. 17B illustrates a medial-lateral view of the proximal tibia bone that is illustrated in FIG. 17A.

FIG. 22 illustrates a distal end view of a fully contained femoral augment according to an illustrated embodiment of the present application.

FIG. 23 illustrates a proximal end view of the fully contained femoral augment according to an illustrated embodiment of the present application.

FIG. 24 illustrates a posterior side view of the fully contained femoral augment illustrated in FIGS. 22 and 23.

FIG. 25 illustrates a medial side view of the fully contained femoral augment illustrated in FIGS. 22 and 23.

FIG. 26 illustrates an anterior side view of the fully contained femoral augment illustrated in FIGS. 22 and 23.

FIG. 27 illustrates a distal end view of a femoral augment structured to accommodate partial containment according to an illustrated embodiment of the present application.

FIG. 28 illustrates a proximal end view of a femoral augment structured to accommodate partial containment according to an illustrated embodiment of the present application.

FIG. 29 illustrates a posterior side view of the femoral augment illustrated in FIGS. 27 and 28.

FIG. 30 illustrates a medial side view of the femoral augment illustrated in FIGS. 27 and 28.

FIG. 31 illustrates an anterior side view of the femoral augment illustrated in FIGS. 27 and 28.

Figure 1:
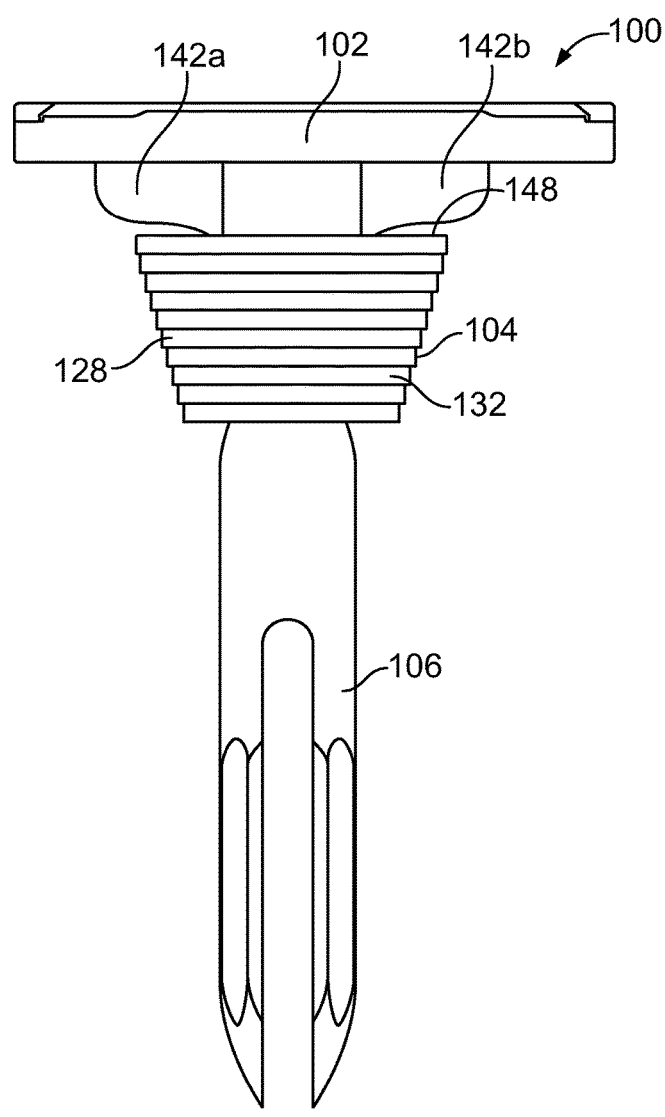
FIG. 1 illustrates as anterior-posterior view of a tibial implant device having a tibial augment according to an embodiment of the present application.
Figure 2:
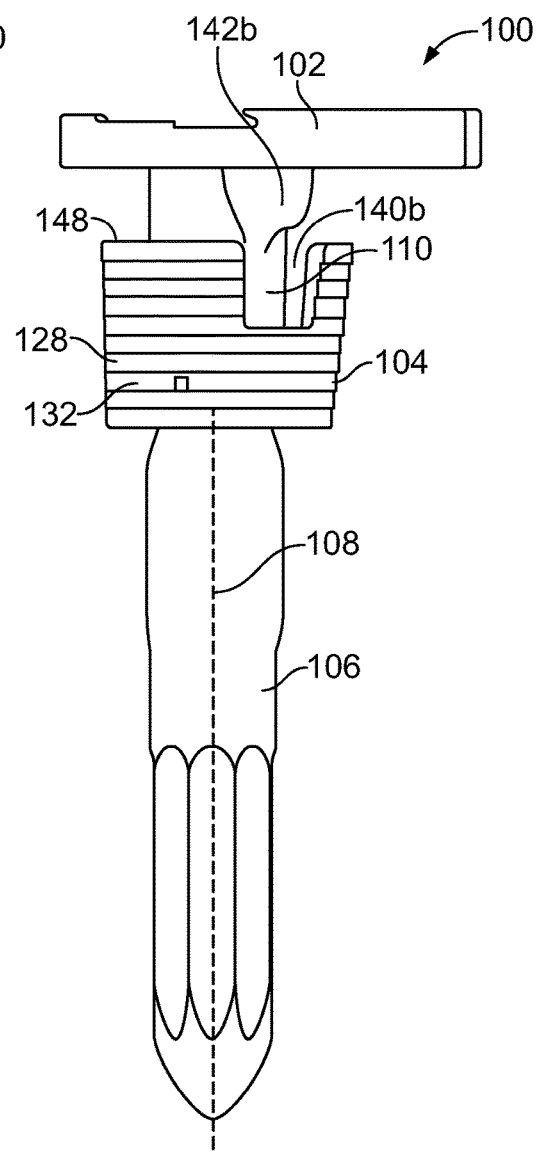
FIG. 2 illustrates a medial-lateral view of the tibial implant device shown in FIG. 1.

The foregoing summary, as well as the following detailed description of certain embodiments of the present application, will be better understood when read in conjunction with the appended drawings in which like reference numbers indicate like features, components and method steps. For the purpose of illustrating the invention, there is shown in the drawings, certain embodiments. It should be understood, however, that the present invention is not limited to the arrangements and instrumentalities shown in the attached drawings.

DESCRIPTION OF ILLUSTRATIVE EMBODIMENTS

Certain terminology is used in the foregoing description for convenience and is not intended to be limiting. Words such as "upper," "lower," "top," "bottom," "first," and "second" designate directions in the drawings to which reference is made. This terminology includes the words specifically noted above, derivatives thereof, and words of similar import. Additionally, the words "a" and "one" are defined as including one or more of the referenced item unless specifically noted. The phrase "at least one of" followed by a list of two or more items, such as "A, B or C," means any individual one of A, B or C, as well as any combination thereof.

FIGS. 1-4 illustrate anterior-posterior, medial-lateral and isometric views, respectively, of an exemplary tibial implant device 100. In the depicted embodiment, the tibial implant device 100 is a tibial articular assembly that includes a tibial (articular) baseplate 102, a tibial augment 104, and a stem 106. The stem 106, which can extend along a central stem axis 108, can be directly or indirectly coupled to the tibial baseplate 102, such as, for example coupled to a tray stem 110. As illustrated in FIG. 4, according to certain embodiments, the tibial implant device 100 can include an offset/angled coupler 112, which can offset at least the central stem axis 108 relative to a central tray stem axis 114 of the tray stem 110. The tibial implant device 100 can also include other components, such as for example, other intramedullary stems and other augments that can be assembled to the tibial implant device 100.

The depicted tibial implant device 100 is structured to be cemented into and through the tibial augment 104 and onto a prepared proximal tibia of a patient. Further, while FIGS. 1-4 illustrate the tibial augment 104 positioned on or about a tibial implant device 100 in a non-implanted state or condition, the tibial augment 104 can be implanted in a bone of the patient prior to implantation of the remainder of the tibial implant device 100. Thus, an inner region 144 of the tibial augment 104 can be sized to receive passage and/or placement of at least a portion of the stem 106 and/or other components of the tibial implant device 100, including, for example the offset/angled coupler 112 and/or the tray stem 110, during implantation of the tibial implant device 100 in a patient.

Figures 5A, 5B:
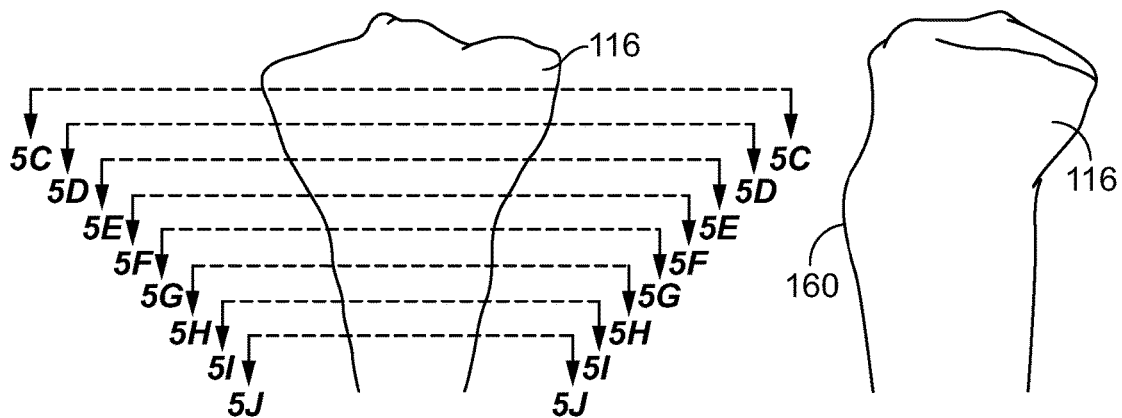
FIGS. 5A and 5C-5J illustrate, respectively, an anterior view of a proximal tibia bone and transverse slice views of the proximal tibia bone, as taken from identified line 5C-5C through identified line 5J-5J.
FIG. 5B illustrates a medial-lateral view of the proximal tibia bone illustrated in FIG. 5A.
Figures 5C, 5D, 5E:
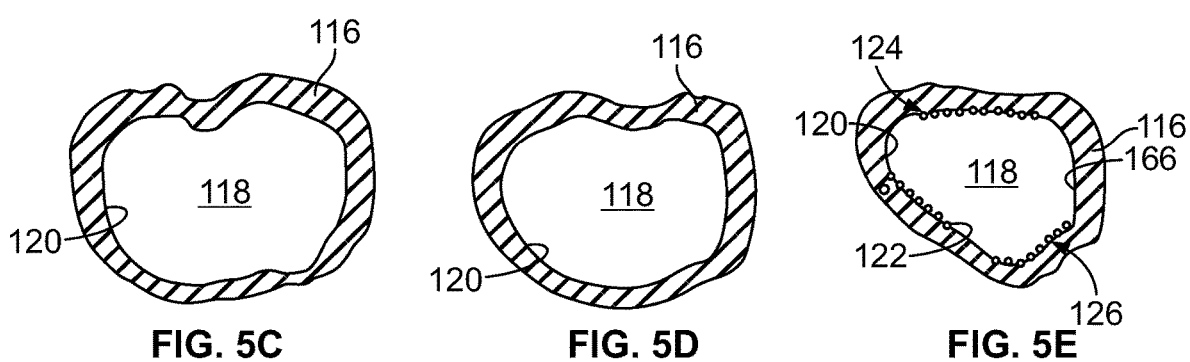
Figures 5F, 5G, 5H:
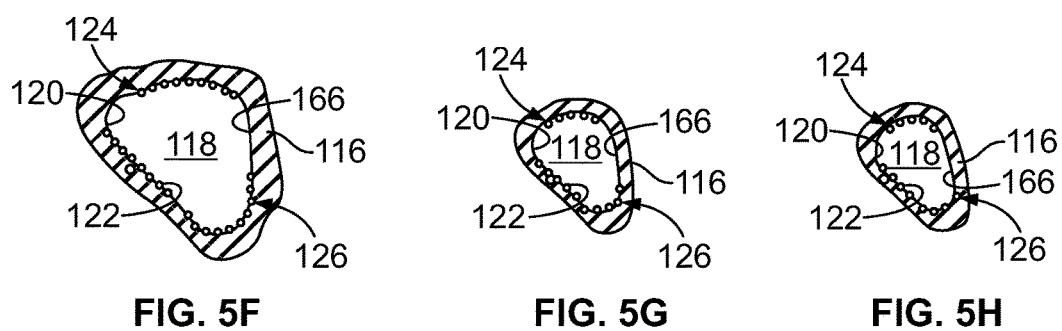
Figures 5I, 5J:
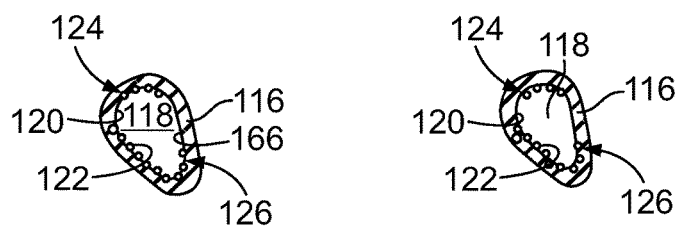
Figure 6:
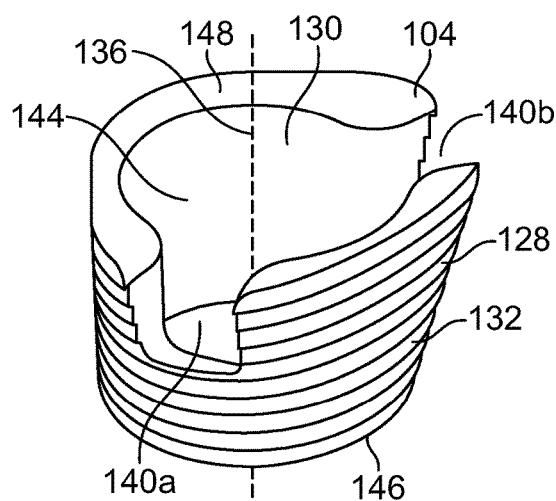
FIG. 6 illustrates a perspective view of a symmetrical tibial augment according to an embodiment of the present application.
Figure 7:
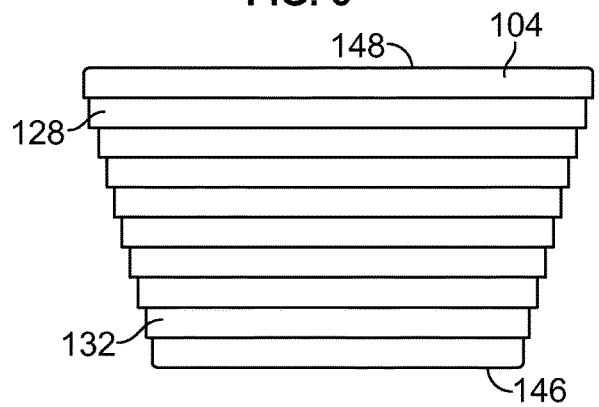
FIG. 7 illustrates a front side view of the symmetrical tibial augment illustrated in FIG. 6.
Figure 8:
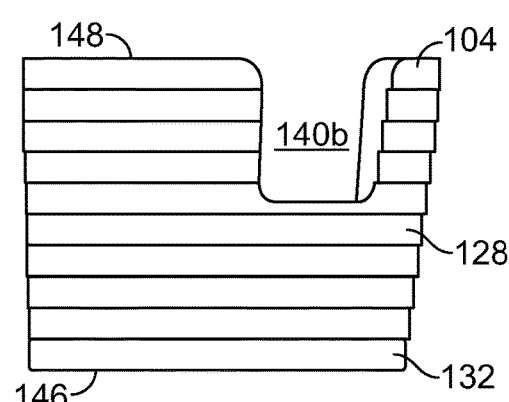
FIG. 8 illustrates a right side view of the symmetrical tibial augment illustrated in FIG. 6.

FIGS. 5A and 5B illustrate anterior and medial-lateral views, respectively, of a proximal tibial bone 116. FIG. 5A also includes transverse slice views of the proximal tibia bone 116, as taken from identified lines 5C-5C through identified line 5J-54J (FIGS. 5C-5J). The proximal tibia bone 116 is oriented in FIG. 5A such that the bone 116 generally tapers inwardly for each sequential transverse slice view, thereby also reducing the size of the intramedullary canal 118. Further, as depicted in each of slices 5E-5E through 5J-5J (FIGS. 5E-5J) of FIG. 5A, the cortical shape of the intramedullary canal 118 can be generally defined by an inner wall 120 of the proximal tibia bone 116 that comprises at least in part, an anterior-medial wall 122 a posterior curvature wall 124, and an anterior-lateral wall 126, the anterior-lateral wall 126 and the posterior curvature wall 124 being separated from each other, at least in part, by the anterior-medial wall 122.

Figure 9:
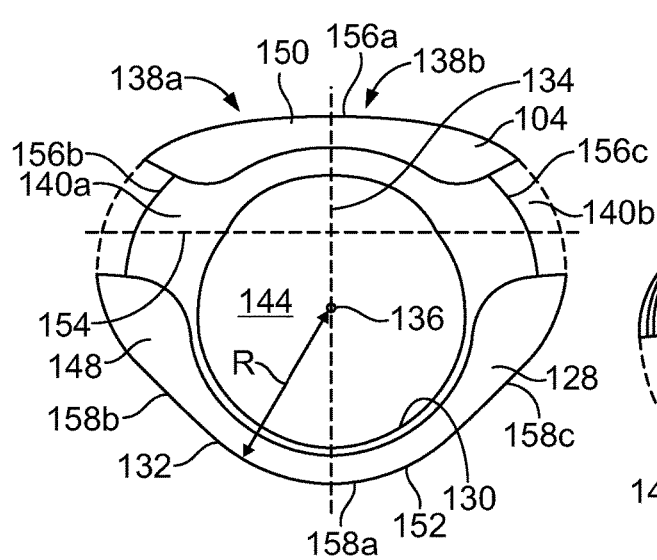
FIG. 9 illustrates a top view of the symmetrical tibial augment illustrated in FIG. 6.

FIGS. 6-10 illustrate an example of a symmetrical tibial augment 104 according to an illustrated embodiment of the present application. A variety of different augments can be used for the tibial augment 104, including, for example, a cone or sleeve augment among other augments. Further, the tibial augment 104, and more specifically an augment wall 128, can have a variety of shapes and sizes, and can have a symmetrical or asymmetrical configuration. For example, as illustrated by at least FIGS. 9 and 10, according to certain embodiments, the augment wall 128 of the tibial augment 104 can be generally symmetrical about a midline 134 that is generally perpendicular to a central longitudinal axis 136 of the tibial augment 104. Thus, as shown in FIG. 9, according to the illustrate embodiment, the midline 134 can generally divide the tibial augment 104 into generally symmetrical first and second sides 138a, 138b. The augment wall 128 can further include at least one opening 140a, 140b that is configured to accommodate placement of a component of the tibial implant device 100. For example, according to the embodiment illustrated in FIGS. 6-10, the tibial augment 104 can include two opening 140a, 140b that are sized to accommodate at least the passage and/or placement of at least a portion of the keel(s) 142a, 142b of the tibial baseplate 102 about or through the opening(s) 140a, 140b. Further, while in the illustrated embodiment the augment wall 128 at the first and second sides 138a, 138b of the tibial augment 104 are depicted as having an opening 140a, 140b, other embodiments can be generally symmetrical with the exception that the augment wall 128 at one of the first and second sides 138a, 138b can contain an opening 140a, 140b, while such an opening 140a, 140b is not present at the other of the first and second sides 138a, 138b.

The augment wall 128 includes an inner portion 130 and an outer portion 132. The inner portion 130 of the augment wall 128 can generally define an inner region 144 of the tibial augment 104. As least a portion of the inner region 144 can extend between a distal end 146 and a proximal end 148 of the tibial augment 104. Additionally, as discussed above, the inner region 144 can be sized to receive placement of at least one or more components of the tibial augment 104, such as, for example, the stem 106, offset/angled coupler 112, and/or tray stem 110 of the tibial baseplate 102, among other components. Additionally, while the surface of the outer portion 132 of the augment wall 128 in the illustrated embodiment has a step appearance or configuration, a variety of other surfaces or surface shapes can also be employed.

The outer portion 132 of the augment wall 128 is shaped to generally fit the cortical shape of a proximal tibia, and more specifically, a portion of the intramedullary canal of the tibia. According to certain embodiments, the outer portion 132 of the augment wall 128 of the tibial augment 104 can be configured such that at least the distal end 146, or diaphyseal end, of the tibial augment 104 conforms to the general shape of the metaphyseal-diaphyseal junction of the tibia bone 116, and at least the proximal end 148 of the tibial augment 104 conforms to the general shape or profile of the metaphyseal region of the tibial bone 116. According to other embodiments, the distal end 146 and/or proximal end 148 can be shaped to provide other cross-sectional shapes that facilitate the ability of the tibial augment 104 to conform to the size and/or shape of at least a portion of the intramedullary canal 118 of the tibia bone 116. Such conforming may not be limited to the physical shape(s) of each section of the outer portion 132 of the augment 104 mating or matching the shape of the adjacent portion of the inner wall 129 of the intramedullary canal 118, but instead can include being shaped to operably contact an adjacent portion of the inner wall 120 of the intramedullary canal 118 while a central longitudinal axis 136 of the tibial augment 104 is aligned with, or at a selected position away from, a reference axis, including, for example, a longitudinal axis of the intramedullary canal 118, the central stem axis 108, and/or the central tray stem axis 114, among other reference axes. Additionally, according to certain embodiments, the portion of the tibial augment 104 that is shaped to generally conform, or fit, to the shape or profile of the metaphyseal region can be located at distance away, in the metaphyseal direction, from the portion of the tibial augment 104 that conforms to the general shape or profile of the metaphyseal-diaphyseal junction that is about the same as the distance between the metaphyseal region and metaphyseal-diaphyseal junction of the tibia bone 116.

Shaping the tibial augment 104 to generally conform to, or accommodate, changes and/or variances in the shape of the intramedullary canal 118 of the tibia bone 116, can prevent or minimize the extent to which the tibial augment 104 is subjected to unequal loading conditions. Further, by shaping different portions or areas of the tibial augment 104, as well as other augments herein, to generally conform to or otherwise accommodate the shape of at least an adjacent inner wall of the associated bone canal or cavity, the generally anatomically shaped augments discussed herein, including the tibial augment 104, 104', and the below-discussed femoral augment 206, 206', can reduce the impact forces on the corresponding articular implant-bone interface by distributing such forces or loads over a relatively larger surface area. More specifically, for example, such conforming configurations of the augments 104, 104', 206, 206' can improve resistance to torsional stress by equally distributing such forces circumferentially.

Further, such variations among and/or along at least the augment wall 128 of the tibial augment 104 can improve flexibility in the placement of the tibial augment 104, and thus reduce or minimize the tibial augment 104 from hindering the ability to position an associated articular component relative to a joint line, while also not hindering joint balance (flexion-extension balance) and rotation of each component relative to the patella-femoral joint.

To generally accommodate the cortical shape(s) of the intramedullary canal 118 of the tibia bone 116, including, for example, the shape at both the metaphyseal-diaphyseal junction and at metaphyseal region of the tibial bone 116, as well m the shapes therebetween, different areas or sides of the outer portion 132 of the augment wall 128 can have different shapes. Additionally, the shapes along such different areas or sides of the outer portion 132 of the augment wall 128 can also vary between the distal and proximal ends 146, 148 of the tibial augment 104. Such variances or inconsistencies among and/or along the sides or areas of the tibial augment 104 can preclude the augment wall 128 of the tibial augment 104 from having a generally uniform cylindrical or conical shape.

Figure 10:
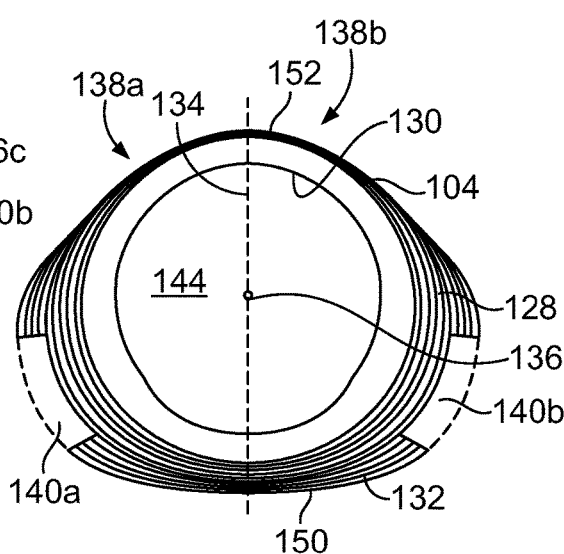
FIG. 10 illustrates a bottom view of the symmetrical tibial augment illustrated in FIG. 6.

Referencing FIGS. 9-10, according to certain embodiments, the augment wall 128 of the tibial augment 104 can include a first, or posterior curvature, portion 150 and a second, or anterior-medial, portion 152 that are separated from each other by at least a transversal axis 154 that is at least perpendicular to the midline 134. Additionally, in the illustrated embodiment, at least a portion of posterior curvature portion 150 has a shape that is different than a corresponding portion of the anterior-medial portion 152. For example, as shown by the top view of the proximal end 148 of the tibial augment 104 in FIG. 9, the posterior curvature portion 150 can include a generally flat section 156a that transitions into rounded end sections 156b, 156c, while the anterior-medial portion 152 can include a rounded section 158a that transitions into generally flat sections 158b, 158c. Such differences in shapes, and the resulting dissimilar profiles, are depicted by at least FIGS. 8 and 10 at least in the region around the proximal end 148 of the tibial augment 104. As demonstrated by at least slices 11D-11D and 11E-11E from FIG. 11A, such differences in the shapes of the posterior curvature and anterior-medial portions 150, 152 of the tibial augment 104 can facilitate the ability of the tibial augment 104 to generally conform to the shape of at least the adjacent posterior curvature wall 126 and the anterior-medial wall 122, respectively, of the inner wall 120 of the intramedullary canal 118. Additionally, as indicated by slice 11D-11D (FIG. 11D) from FIG. 11A, a portion of the anterior-medial portion 152 and/or the posterior curvature portion 150 can contact other portions of the inner wall 120 of the intramedullary canal 118, including, for example, the lateral wall 166.

Figure 11A:
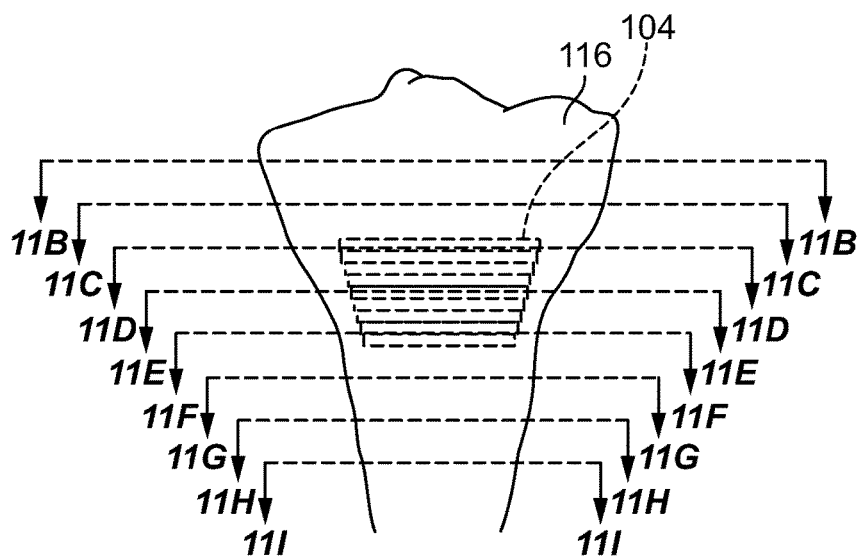
FIGS. 11A-11I illustrate, respectively, the anterior view of the proximal tibia bone and slice views from FIGS. 5A-5J, but with m exemplary symmetrical tibial augment of the present application implanted in the intramedullary canal.
Figure 11B:
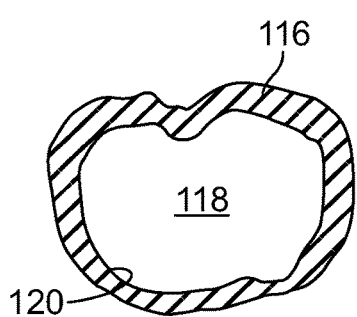
Figure 11C:
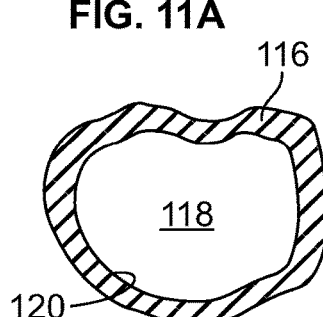
Figure 11D:
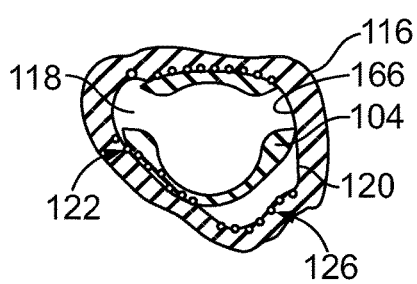
Figure 11E:
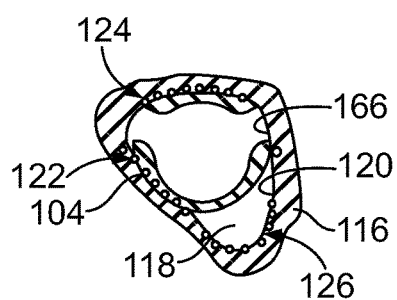
Figure 11F:
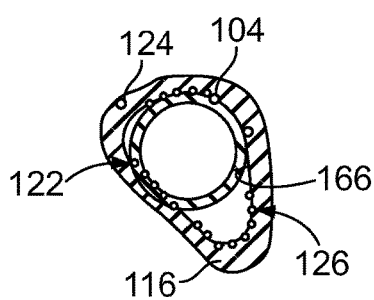
Figure 11G:
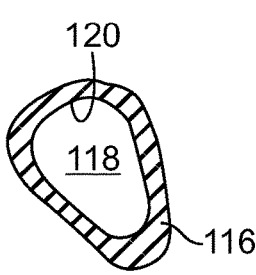
Figure 11H:
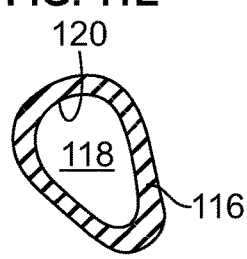
Figure 11I:
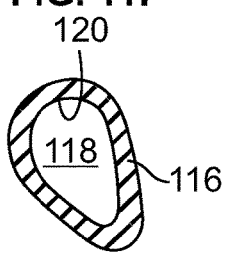
Figure 14:
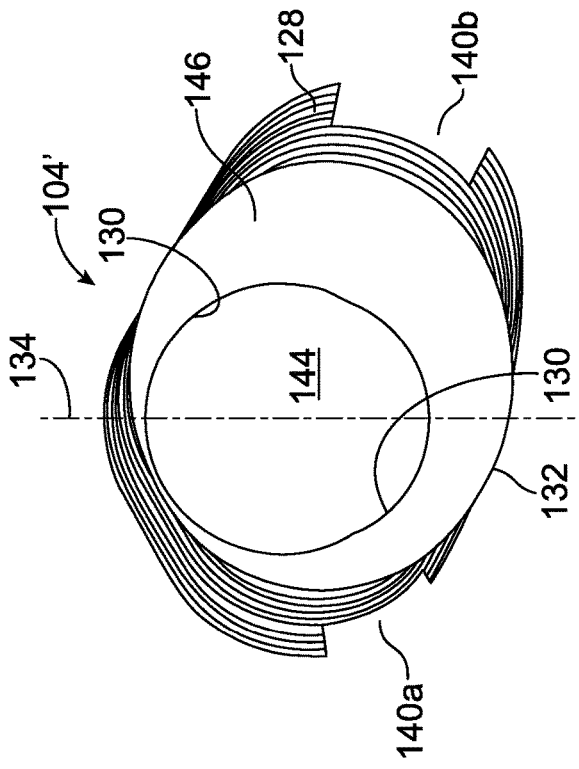
FIG. 14 illustrates a bottom view of the asymmetrical tibial illustrated in FIG. 13.
Figure 13:
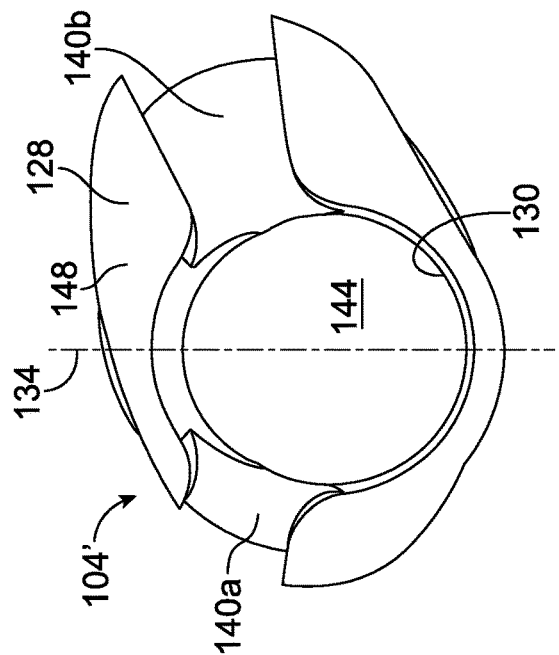
FIG. 13 illustrates a top view of an asymmetrical tibial augment according to an illustrated embodiment of the present application.
Figure 16:
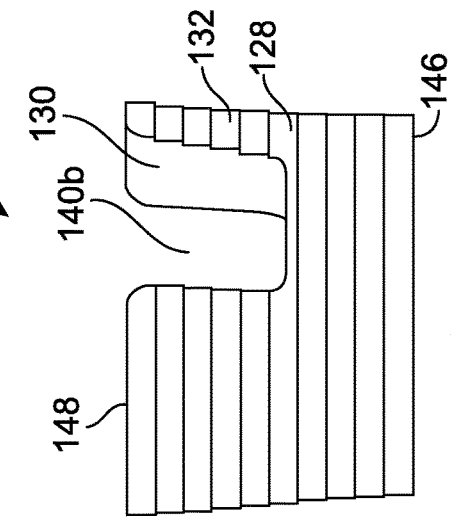
FIG. 16 illustrates a right side view of the asymmetrical tibial illustrated in FIG. 13.
Figure 15:
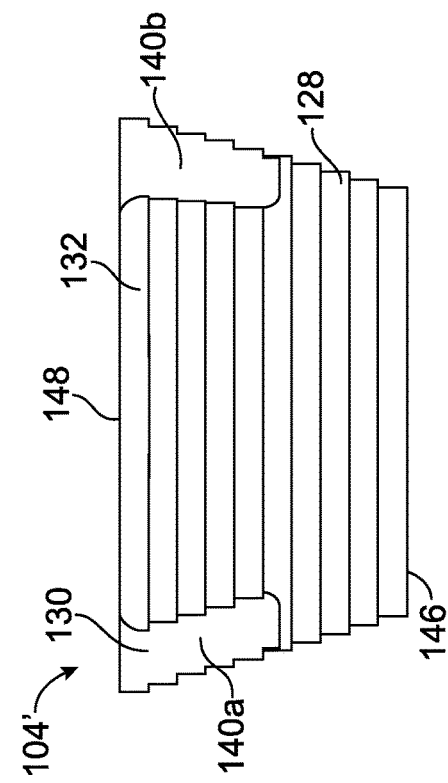
FIG. 15 illustrates a front view of the asymmetrical tibial illustrated in FIG. 13.

The different shapes of the posterior curvature and anterior-medial portions 150, 152 can alter or vary between the distal and proximal ends 146, 148 along the augment wall 128 so that the outer position 132 of the augment 104 generally conforms to changes in shape along the inner wall 120 of the intramedullary canal 118 of the tibia bone 116, as depicted each of slice views 5C-5C through 5J-5J from FIGS. 5A and 11B-11B through 11I-11I (FIGS. 11B-11I) from FIG. 11A. According to the illustrated embodiment shown in at least FIGS. 6-11, such changes in shape in the inner wall 120 of the intramedullary canal 118, and corresponding changes in shape along least the posterior curvature and anterior-medial portions 150, 152 of the augment wall 128, can result in the posterior curvature and anterior-medial portions 150, 152 generally having similar shapes at the distal end 146 of the tibial augment 104, as shown, for example, by FIG. 10 and slice E-E in FIG. 11. Such similarities in the shape of the posterior curvature and anterior-medial portions 150, 152 can, for example, provide the augment wall 128 with a generally circular, semicircular, or slightly oval shape at the distal end 146 of the tibial augment 104. However, again, the particular shape(s) of the augment wall 128 at the distal end 140 of the tibial augment 104 can be configured or selected to generally conform to the metaphyseal-diaphyseal junction of the tibia bone 116.

FIGS. 12A-12D further illustrate the symmetrical tibial augment 104 that is shaped to conform to the shape of the cortical shape of the bone 116, and more specifically, in the illustrated embodiment, to the adjacent shape of the intramedullary canal 118. For example, as shown in FIG. 12C, the proximal end 148 of the tibial augment 104 is shaped to generally conform to the general shape or profile of adjacent portions of the metaphyseal region of the tibial bone 116. Further, as shown in FIGS. 12C and 12D, the region around the anterior-lateral wall 126, and moreover, in the region of the tibial tubercle 160, can often be covered, at least in part, by the anterior aspect of a transversely resected portion of the proximal tibia bone 116. Such coverage can prevent the tibial augment 104 from having direct access inferior-superior to the cancellous area 182 that can be present behind the tibial tubercle 160. Yet, without direct access or special instrumentation, preparation, as well as placement of the tibial augments that had the anatomical shapes disclosed herein, at such a location can be difficult.

Referencing FIGS. 13-16, in at least certain instances, patients can have an abnormality in the shape and/or size of the intramedullary canal 118 and/or can require enhanced support from a tibial augment 104'. In such situations, the tibial augment 104' can have an asymmetrical configuration about the midline 134, as shown in at least FIGS. 13 and 14. Such as asymmetrical configuration can increase a thickness of the augment wall 128 between at least certain sections of the inner and outer portions 130, 132 of the augment wall 128. For example, compared to slices 11D-11D, 11E-11E, and 11F-11F (FIGS. 11D-11F) from FIG. 11A, the asymmetrical tibial augment 104' shown in slice views from 17E-17E, 17F-17F, and 17G-17G (FIGS. 17E-17G) from FIG. 17A has and increased thickness in the augment wall 128 at least in the vicinity of the lateral wall 166 portion of the inner wall 120 of the intramedullary canal 118. However, according to certain embodiments, such increases in the thickness of the augment wall 128 and/or increases of the augmented wall 128 in certain locations can be limited due to the previously discussed limitations associated with the cancellous area 162 behind the tibial tubercle 160.

Figure 18:
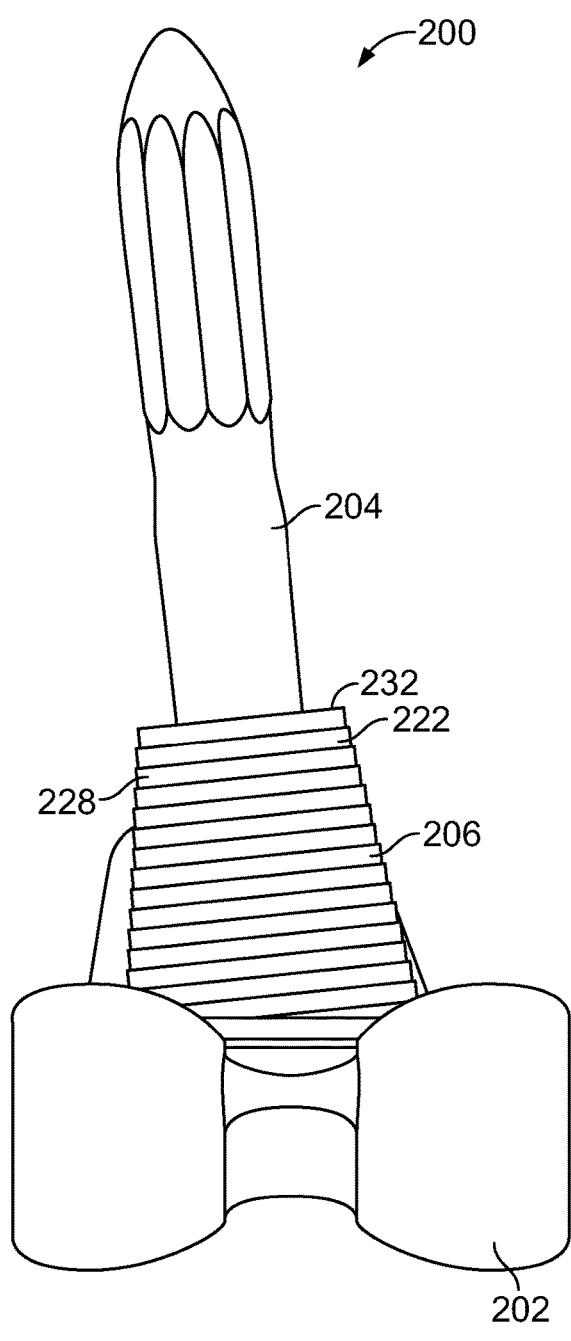
FIG. 18 illustrates a posterior-anterior view of a femoral implant device having a femoral articular component, an intramedullary stem, and a femoral augment according to an illustrated embodiment of the present application.
Figure 19:
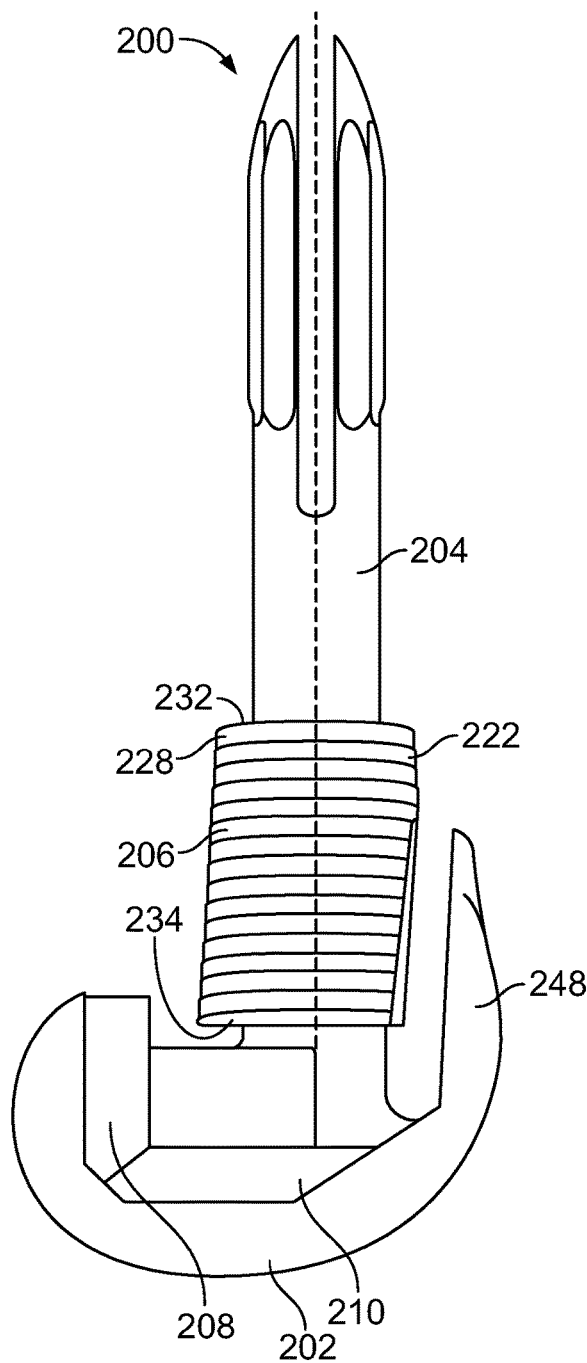
FIG. 19 illustrates a medial-lateral view of the femoral implant device shown in FIG. 18, which is depicted as further including distal and posterior augments.
Figure 21:
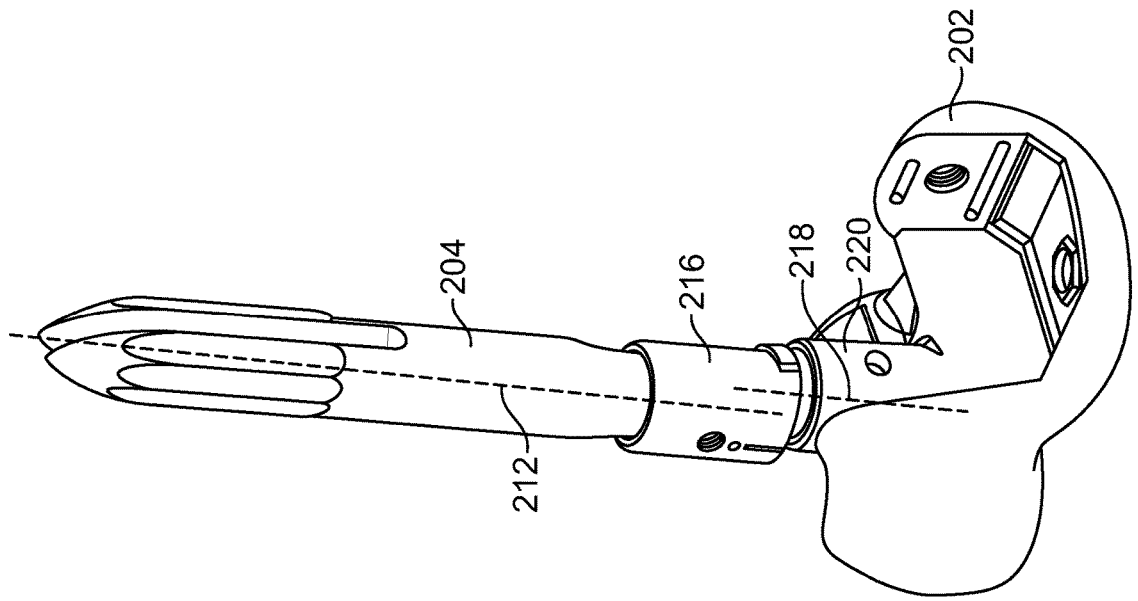
FIG. 21 illustrates an isometric view of the femoral implant having an offset/angled coupler.
Figure 20:
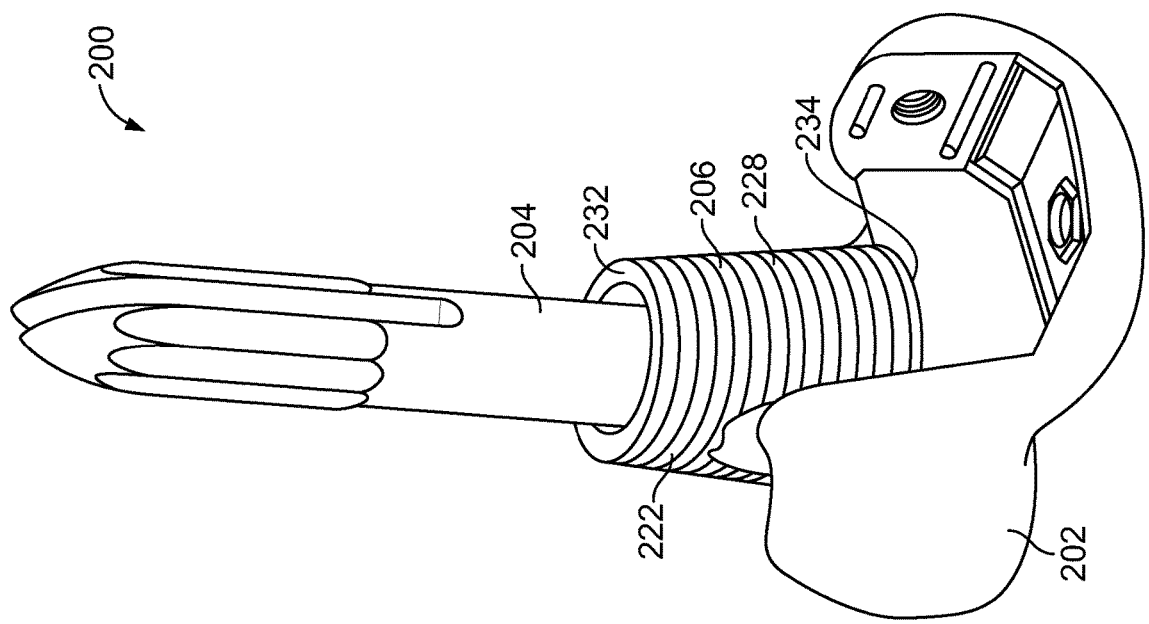
FIG. 20 illustrates an isometric view of the femoral implant device shown in FIG. 18.

FIGS. 18-20 illustrate posterior-anterior, medial-lateral, and isometric views, respectively, of a femoral implant device 200. According to an illustrated embodiment of the present application, the femoral implant device 200 includes a femoral articular component 202, an intramedullary stem 204, and a femoral augment 206. Additionally, as shown in FIG. 19, according to certain embodiments, the femoral implant device 200 can also include a distal augment 208 and/or a posterior augment 210. The stem 204, which can extend along a central stem axis 212, can be directly or indirectly coupled to the femoral articular component 202, such as, for example, coupled to a component stem 220 of the femoral articular component 202, as shown in FIG. 21. As illustrated in FIG. 21, according to certain embodiments, the femoral implant device 200 can include an offset/angled coupler 216, which can offset at least the central stem axis 212 relative to a component stem axis 218 of the component stem 220.

The depicted femoral implant device 200 is structured to be cemented into and through the femoral augment 206 and onto a prepared distal femur of a patient. Further, while FIGS. 18-21 illustrate the femoral augment 206 positioned on or about a femoral implant device 200 in a non-implanted state or condition, the femoral augment 200 can be implanted in a bone of the patient prior to implantation of the remainder of the femoral implant device 200. Thus, an inner region of the femoral augment 206 can be sized to receive passage and/or placement of at least a portion of the stent 204 and/or other components of the femoral implant device 200, including, for example, the offset/angled coupler 216 and/or the component stent 220, during implantation of the femoral implant device 200 in a patient.

FIGS. 23-26 illustrate an example of a fully contained femoral augment 206 according to an illustrated embodiment of the present application. A variety of different augments can be used for the femoral augment 206, including, for example, a cone or sleeve augment, among other augments. Further, the femoral augment 206 can have a variety of shapes and sizes. The femoral augment 200 can include an augment wall 222 that extends about a central axis 224 of the femoral augment 206. The augment wall 222 has an inner portion 226 and an outer portion 228. The inner portion 226 of the augment wall 222 can generally define an inner region 230 of the femoral augment 206. At least a portion of the inner region 230 can extend between a distal end 232 and a proximal end 234 of the femoral augment 206. The inner region 230 can be sized to receive placement of at least one or more components of the femoral augment 206, such as, for example, the stem 204, offset/angled coupler 216, and/or component stem 220 of the femoral articular component among other components. For example, according to certain embodiments, the inner region 230 is sized to receive placement of at least the junction between the stem 204 and the component stem 220.

The outer portion 228 of the augment wall 222 can be shaped to generally fit the cortical shape of a distal femur, and more specifically, of a portion of the intramedullary canal of the femur. Thus, according to certain embodiments, a diaphyseal, or distal end 232, of the femoral augment 206 can be shaped to generally conform to the general shape of the metaphyseal-diaphyseal junction. The opposing proximal end 234 of the femoral augment 206 can be configured to conform to the general shape or profile of the metaphyseal region of the femoral bone. According to other embodiments, the distal end 232 and/or proximal end 234 can be shaped to provide other cross-sectional shapes that facilitate the ability of the femoral augment 206 to conform to the size and/or shape of at least a portion of the intramedullary canal of the femur. Such conforming may not be limited to the physical shape(s) of each section of the outer portion 228 of the augment mating or matching the shape of the adjacent portion of the inner wall of the intramedullary canal of the femoral bone, but instead can include being shaped to operably contact adjacent portion of the inner wall of the intramedullary canal while a central axis 224 of the femoral augment 206 is aligned with, or at a selected position away from, a reference axis, including, for example, a longitudinal axis of the intramedullary canal of the femur, the central stem axis 212, and/or the component stem axis 218, among other reference axes. Additionally, the portion of the femoral augment 206 that is shaped to generally conform to the shape or profile of the metaphyseal region can be located at distance away, generally in the distal direction, from the portion of the femoral augment 206 that conforms to the general shape or profile of the metaphyseal-diaphyseal junction that is about the same as the distance between the metaphyseal region and metaphyseal-diaphyseal junction of the tibia.

Similar to the tibial augment 104, 104', shaping the femoral augment 206 to generally conform to, or accommodate, changes and/or variances in the shape of the intramedullary canal of the femur can prevent or minimize the extent to which the femoral augment 206 is subjected to unequal loading conditions. Further, again, by shaping different portions or areas of the femoral augment 206, as well as other augments herein, to generally conform to or otherwise accommodate the shape of at least an adjacent inner wall of the associated bone canal or cavity, the generally anatomically shaped augments 104, 104', 206, 206', discussed herein can reduce the impact forces on the corresponding articular implant-bone interface by distributing such forces or loads over a relatively larger surface area. More specifically, for example, such conforming configurations of the augments 104, 104', 206, 206' can improve resistance to torsional stress by equally distributing such forces circumferentially.

To generally accommodate the cortical shape(s) of the medullary canal of the femur, including, for example, the shape at both the metaphyseal-diaphyseal junction and at metaphyseal region of the femur, as well as the shape therebetween, different areas or sides of the outer portion 228 of the augment wall 222 can have different shapes. Additionally, the shapes along such different areas or sides of the outer portion 228 of the augment wall 222 can also vary between the distal and proximal ends 232, 234 of the femoral augment 206. Such variances or inconsistencies among and/or along the sides or areas of the femoral augment 206 can preclude the augment wall 222 of the femoral augment 206 from having a generally uniform cylindrical or conical shape.

Referencing FIGS. 22-26, according to certain embodiments, the outer portion 228 of the augment wall can include a recess or relief 236. As shown by at least FIG. 26, according to the illustrated embodiment, the relief 236 can extend along a portion of the augment wall 222, such as, for example, extending from the proximal end 234 to a region generally adjacent to the distal end 232 of the femoral augment 206. However, according to other embodiments, the relief 236 can extend between, and through, the proximal end 234 and/or the distal end 232 of the femoral augment 206. In the illustrated embodiment, the relief 236 can have one or more sidewalls 238 and a base wall 240. For example, as shown in FIG. 23, the one or more sidewalls 238 can include a first sidewall 238a and a second sidewall 238b. The first and second sidewalls 238a, 238b can be angled such that the first and second sidewalls 238a, 238b converge toward each other from generally opposite directions and/or angles. For example, in the illustrated embodiment, the first and second sidewalls 238a, 238b can each extend from opposing first ends 242a, 242b, and converge toward each other so as intersect or be generally in proximity to each other at second ends 244a, 244b of the first and second sidewalls 238a, 238b. Further, in the illustrated embodiment, the second ends 244a, 244b can be adjacent to, or generally form, an augment flange 246 that projects away from the first and second sidewalls 238a, 238b.

As indicated by FIG. 25, according to certain embodiments, the first and second sidewalls 238a, 238b can also be angled or tapered, and thus non-parallel to a longitudinal central axis 224 of the femoral augment 206. For example, as shown in the embodiment depicted in FIG. 26, the portion of the first and second sidewalls 238a, 238b at the proximal end 234 of the augment wall 222 can be separated from the central axis 224 of the femoral augment 206 by a distance that is smaller than the distance between the central axis 224 and the vicinity of the intersection of the first and second sidewalls 238a, 238b and the base wall 240. However, according to other embodiments, the first and second sidewalls 238a, 238b can be generally parallel to the central axis 224 of the femoral augment 206.

As shown by at least FIGS. 19 and 20, according to the illustrated embodiment, the relief 236 can be shaped such that, when the femoral augment 206 is operably positioned on the femoral implant device 200, the relief 236 is generally parallel to the bone facing side of the anterior flange 248 of the femoral implant device 200. Such a shape can at least assist in adjustable rotational displacement of the femoral augment 206 relative to the femoral implant device 200, and more particularly, of the anterior flange 248 (FIG. 19) relative to the femoral augment 206. Such rotation adjustment can also be facilitated by the angular orientation of the first and/or second sidewalls 238a, 238b of the augment wall 222. For example, as indicated by the exemplary femoral augments 206, 206' shown in FIG. 23 and FIG. 28, the first sidewall 238a can be oriented to facilitate that ability to adjust the angular position of the femoral augment 206 relative to other components of the femoral implant device 200, such as, for example, relative to the anterior flange 248, by about 20 degrees, among other degrees of rotational freedom. Thus, for example, such rotational displacement can, when the femoral implant device 200 is implemented in a patient, allow for selective adjustment in the distance between the first end 242a of the first sidewall 238a and the anterior flange 248.

The rotational freedom provided by incorporation of the relief 236 and the associated adjustment in the position of the femoral augment 206 relative to the anterior flange 248 can assist in the femoral augment being adapted to accommodate rotational variation in the geometry of the intramedullary canal of the femur. Moreover, the relief 236 can assist in enhancing the flexibility as to the orientation at which the femoral augment 206 can be implanted in the intramedullary canal so as to further enhance the ability of the femoral augment 206 to conform or otherwise accommodate the particular shape of the intramedullary canal which also minimizing or preventing the position of the femoral augment 206 from impeding the positioning or operation of other components of the femoral implant device 200. For example, the rotational freedom of the femoral augment 206 that is provided by, at least in part, the inclusion of the relief 236 can enhance the ability to position the femoral augment 206 to accommodate for rotational variation in the shape of the intramedullary canal while also not preventing the femoral implant device 200, such a femoral articular component, from being positioned at a particular transverse rotational location.

FIGS. 27-31 illustrate a femoral augment 206' that is adapted to accommodate larger components, or collections of components, in the inner region 230' of the augment 206'. For example, the femoral augment 206' depicted in FIGS. 27-31 can be adapted to receive in the inner region one or more of the stem 204, component stem 220, and/or the offset/angled coupler 216, among other components. According to such an embodiment, the relief 236 or augment flange 246, if any, can include one or more tear lines or relief areas 250 that are adapted to open, break through, or tear the augment wall 222, or otherwise relieve at least a portion of the augment 206'. Thus, in certain situations, the formation of an opening along one or more of the tear lines or relief areas 250 can provide access to additional space so as to prevent the inner region 230' from restricting or impeding positioning of components of the femoral implant device 200 relative to the femoral augment 206. Thus, unlike the fully contained inner region 230 of the femoral augment 206 shown in FIGS. 23-24, the tear lines or relief areas 250 can allow for the femoral augment 206' to transition from being fully contained to partially contained, which can occur, for example, upon the formation of openings or breakage along the tear line or relief areas 250.

Additionally, in the illustrated embodiments on the femoral augments 206, 206' shown in at least FIGS. 23-31, at least some sides of the of the femoral augments 206, 206' can have different shapes and/or configurations. Further, similar to the tibial augments 104, 104' discussed above, the shape or configurations of those sides can alter, and can alter differently between the proximal and distal ends 232, 234 of the femoral augments 206, 206'. For example, referencing the top views of FIGS. 23 and 28, at the distal ends 232 of the femoral augments 206, 206', the femoral augments 206, 206' can have be generally egg-shape, which can assist in providing different shaped and sized profiles along the augment wall 222 of the femoral augments 206, 206', and shown by a comparison of FIGS. 24 and 26 with FIG. 25, and a similar comparison of FIGS. 29 and 31 with FIG. 30. Further, while the distal end 234 in the illustrated embodiments is shown as being generally egg-shaped, as shown in the FIGS. 22 and 27, the proximal ends 232 of the femoral augments 206, 206' can be generally circular. Thus, the transitions between, and the associated shapes, of the proximal and distal ends 232, 234 can preclude the femoral augments 200, 200' from having a generally uniform cylindrical or cortical shape. Instead, as previously mentioned such variations in shapes along different portions of the femoral augment 206, 206' can be adapted to enhance the ability of the femoral augment 206, 206' to generally conform to the shape of adjacent portions of the intramedullary canal of the femur.

While the invention has been described In connection with what is presently considered to be the most practical and preferred embodiment, it is to be understood that the invention is not to be limited to the disclosed embodiment(s), but on the contrary, is intended to cover various modifications and equivalent arrangements included within the spirit and scope of the appended claims, which scope is to be accorded the broadest interpretation so as to encompass all such modifications and equivalent structures as permitted under the law. Furthermore it should be understood that while the use of the word preferable, preferably, or preferred in the description above indicates that feature so described may be more desirable, it nonetheless may not be necessary and any embodiment lacking the same may be contemplated as within the scope of the invention, that scope being defined by the claims that follow. In reading the claims it is intended that when words such as "an," "at least one" and "at least a portion" are used, there is no intention to limit the claim to only one item unless specifically stated to the contrary in the claim. Further, when the language "at least a portion" and/or "a portion" is used the item may include a portion and/or the entire item unless specifically stated to the contrary.

The invention claimed is:

1. A femoral augment for implantation with an orthopedic implant device in a bone, the femoral augment comprising:
   an augment wall having an outer portion and an inner portion, the inner portion defining an inner region of the augment, the inner region being sized to receive placement therein of a stem of the orthopedic implant device, and the outer portion having an outer surface;
   wherein the inner region extends along a central axis;
   wherein the outer portion has a proximal end, a distal end, an anterior side, a posterior side, a medial side, and a lateral side;
   wherein the proximal end has a first size and a first shape;
   wherein the distal end has a second size, which is different from the first size, and a second shape, which is different from the first shape;
   wherein the medial side or the lateral side extends at a first oblique angle, relative to the central axis;
   wherein the anterior side extends at a second oblique angle, relative to the central axis;
   wherein the first oblique angle is different from the second oblique angle;
   wherein at least one of the first shape and the second shape is an oval shape;
   wherein the augment wall comprises a relief, which is a portion of the augment wall that has a reduced thickness as compared to other portions of the augment wall, the relief defining and forming the outer surface of the portion of the augment wall where the relief is located, the relief comprising at least a first sidewall and a second sidewall that extend over the outer surface of the augment wall;
   wherein the augment wall has a first thickness, the reduced thickness of the relief being less than the first thickness;
   wherein the first sidewall and the second sidewall both are formed contiguous with the proximal end and extend away from the proximal end in a direction of the central axis; and
   wherein the first sidewall and the second sidewall are angled relative to each other, such that the first and second sidewalls are not parallel to each other.

2. The femoral augment of claim 1, wherein an angle, measured external to the augment, between the first sidewall and the second sidewall is greater than 180° and the relief interrupts the oval shape.

3. The femoral augment of claim 2, wherein a thickness of the augment wall, as measured radially between the inner portion and the outer portion of the augment, is reduced where the relief interrupts the oval shape.

4. The femoral augment of claim 2, wherein the first sidewall has an outer surface that is planar and the second sidewall has an outer surface that is planar.

5. The femoral augment of claim 1, wherein:
the first sidewall has a tapered shape, such that a width of the first sidewall is greatest at the proximal end and decreases along the central axis; and/or
the second sidewall has a tapered shape, such that a width of the first sidewall is greatest at the proximal end and decreases along the central axis.

6. The femoral augment of claim 1, wherein:
the first shape and the second shape are both oval shaped but the second shape is different from the first shape in both size and shape; or
the first oblique angle is a first acute angle and the second oblique angle is a second acute angle, which is less than the first acute angle; or
a posterior portion of the distal end has a lesser thickness than an anterior portion of the distal end; or
the outer portion includes a set of stepped features and each stepped feature in the set corresponds to a different cross-section of an intramedullary canal.

7. The femoral augment of claim 1, wherein the first sidewall and the second sidewall extend in the direction of the central axis to a base wall that is spaced apart from the distal end and extends in a continuous and uninterrupted manner between the first and second sidewalls.

8. The femoral augment of claim 7, wherein:
the base wall has a terminal first end and a terminal second end;
the base wall extends in a continuous and uninterrupted manner around a perimeter formed by the first and second sidewalls, from the terminal first end to the terminal second end;
the terminal first end is defined at a position that is both at and intersecting the proximal end; and
the terminal second end is defined at a position that is both at and intersecting the proximal end.

9. The femoral augment of claim 1, wherein the relief comprises, positioned between the first sidewall and the second sidewall in a circumferential direction of the augment, an augment flange that extends away from the proximal end along the central axis to have a same length, as measured in the direction of the central axis, as the first and second sidewalls.

10. The femoral augment of claim 9, wherein the augment flange has an outer surface that is planar.

11. The femoral augment of claim 10, wherein the planar outer surface of the augment flange has a rectangular shape.

12. The femoral augment of claim 9, wherein the augment flange is oriented at an angle, relative to the first and second sidewalls, such that an external angle measured between the first sidewall and the augment flange is greater than 180° and an external angle measured between the second sidewall and the augment flange is greater than 180°.

13. The femoral augment of claim 9, wherein the first sidewall, the second sidewall, and the augment flange extend in the first of the central axis to a base wall that is spaced apart from the distal end and extends in a continuous and uninterrupted manner between the first sidewall, the augment flange, and the second sidewall.

14. The femoral augment of claim 13, wherein:
the base wall has a terminal first end and a terminal second end;
the base wall extends in a continuous and uninterrupted manner around a perimeter formed by the first sidewall, the augment flange, and the second sidewall, from the terminal first end to the terminal second end;
the terminal first end is defined at a position that is both at and intersecting the proximal end; and
the terminal second end is defined at a position that is both at and intersecting the proximal end.

15. A femoral implant system comprising:
an orthopedic implant device including a stem, wherein the stem is configured for insertion into an intramedullary canal of a femur; and
the femoral augment of claim 1.

16. The femoral implant system of claim 15, wherein the orthopedic implant device further includes:
an articular component; and
an angled coupler connecting the stem to the articular component.

17. The femoral implant system of claim 16, wherein the inner portion surrounds the angled coupler.

18. The femoral implant system of claim 15, wherein an angle, measured external to the augment, between the first sidewall and the second sidewall is greater than 180° and the relief interrupts the oval shape.

19. The femoral implant system of claim 15, wherein the relief is configured to accommodate rotational displacement of the augment relative to the stem of the orthopedic implant device.

20. The femoral implant system of claim 15, wherein the relief is positioned adjacent to an anterior flange of the orthopedic implant device.

* * * * *